United States Patent [19]

Eberhardt

[11] Patent Number: 4,535,241
[45] Date of Patent: Aug. 13, 1985

[54] MEASURING THE CONCENTRATION OF GASEOUS HYDROGEN FLUORIDE

[75] Inventor: John E. Eberhardt, Sans Souci, Australia

[73] Assignee: Australian Atomic Energy Commission, New Wales, Australia

[21] Appl. No.: 444,900

[22] PCT Filed: Apr. 8, 1982

[86] PCT No.: PCT/AU82/00055
§ 371 Date: Nov. 17, 1982
§ 102(e) Date: Nov. 17, 1982

[87] PCT Pub. No.: WO82/03687
PCT Pub. Date: Oct. 28, 1982

[30] Foreign Application Priority Data

Apr. 13, 1981 [AU] Australia ............................ PE8425
May 13, 1981 [AU] Australia ............................ PE8858

[51] Int. Cl.³ ........................................... G01N 21/35
[52] U.S. Cl. ................................... 250/339; 250/338; 250/343; 356/437
[58] Field of Search ............... 356/437; 250/343, 345, 250/346, 339, 338

[56] References Cited

U.S. PATENT DOCUMENTS 2,930,893 3/1960 Capenter et al. ................... 250/339
3,998,557 12/1976 Javan ................................... 356/434
4,061,918 12/1977 Preier et al. ......................... 250/343

FOREIGN PATENT DOCUMENTS

EP26046 8/1980 Australia .
2171519 9/1973 France .
2304922 3/1976 France .
1475909 6/1977 United Kingdom .

OTHER PUBLICATIONS

Laguna et al, "Direct Measurement of the Absorption Coefficient for the $P_1(7)$ Transition in HF", J. App. Phys., 46 (11), Nov. 1975, pp. 5049-5050.

Primary Examiner—Alfred E. Smith
Assistant Examiner—Carolyn E. Fields
Attorney, Agent, or Firm—Ladas & Parry

[57] ABSTRACT

Method and apparatus for quantitatively determining the concentration of gaseous hydrogen fluoride in a medium containing gaseous hydrogen fluoride. The apparatus has one or two lasers (1) (2) which provides a beam (11) having two frequencies, a first frequency which is absorbed by gaseous hydrogen fluoride and a second frequency which is substantially unabsorbed by low pressure gaseous hydrogen fluoride and less absorbed than the first frequency by high pressure gaseous hyrogen fluoride or gaseous hydrogen fluoride plus other gases or vapors. Detectors (12) (15) detect the beam transmitted through the medium and calculator (18) determines the concentration from the outputs of the detectors (12) (15). The preferred lasers (1) (2) are infra red helium-neon lasers.

13 Claims, 4 Drawing Figures

MEASURING THE CONCENTRATION OF GASEOUS HYDROGEN FLUORIDE

The present invention relates to improvements in and relating to a method and apparatus for the determination of concentration of gaseous hydrogen fluoride.

BACKGROUND ART

Gaseous hydrogen fluoride is evolved in several industrial processes, the most important of which are aluminium smelting and enrichment of uranium via uranium hexafluoride. As hydrogen fluoride is a serious atmospheric pollutant, it is important that the amount of hydrogen fluoride released into the atmosphere is monitored to control its release in such processes. Gaseous hydrogen fluoride may also be generated by power stations and in brickworks.

Whilst the following description is directed to monitoring hydrogen fluoride evolution in the aluminium smelting industry, it will be apparent that the method and apparatus of the present invention can be employed to detect and determine gaseous hydrogen fluoride in any medium with significant transmission at the appropriate frequencies.

Present proposals for aluminium smelting in the Hunter Valley of N.S.W. envisage a large increase in aluminium output ("Pollution control in the Hunter Valley with Particular Reference to Aluminium Smelting" N.S.W. State Pollution Control Commission (hereinafter referred to as SPCC) Report, August 1980).

In the production of aluminium, alumina powder is electrolysed in molten cryolyte ($Na_3AlF_6$) to aluminium metal and oxygen which combines with the carbon of the carbon anodes to produce carbon monoxide and carbon dioxide. During the process about 20 kg of fluoride, mainly in the form of gaseous hydrogen fluoride is emitted per tonne of aluminium produced.

Aluminium production is carried out in long pot-rooms, which are typically 800×25 m and which each generally contain about 100 electrolytic cells. Hoods over the electrolytic cells draw off approximately 97.5% of the emitted gaseous hydrogen fluoride and exhaust it through dry scrubbers which retain 99.9% hydrogen fluoride, thence to stacks. The main source of fluoride pollution is gaseous hydrogen fluoride escaping from the cell hoods, particularly when anodes are changed. The gaseous hydrogen fluoride is released from the roof vents of the pot-room as described in the SPCC report, August 1980 supra. The maximum concentration allowed in the pot-rooms on the ground of industrial health is 2 $mg.m^{-3}$. The SPCC have imposed an obligation on the smelter operators to monitor continuously the gaseous hydrogen fluoride concentration in the pot-rooms with levels in the range 40–400 $\mu g.m^{-3}$ as a suggested working range. Monitoring gaseous hydrogen fluoride conveniently and economically has heretofore posed many problems.

Present monitoring methods involve pumping air containing gaseous hydrogen fluoride through heated filters to remove fluoride particulates and then through solutions or lime beds. The calcium fluoride formed is assayed using a fluoride selective electrode. These methods are said to be inconvenient, not suitable for reliable automation, and not very accurate.

Whilst not required at present, it is proposed that the SPCC will require aluminum smelter operators to monitor continuously the scrubber stack emmissions, and the gaseous hydrogen fluoride concentrations at four positions inside and two positions outside the plants. Permissible gaseous hydrogen fluoride levels outside the pot-rooms may be in the range 1–10 $\mu g.m^{-3}$.

Atmospheric pollutants may be monitored by long path length optical absorption measurements as described in "Troposcopic Photochemical and Photophysical Processes", J. N. Pitts and B. J. Finlayson-Pitts; "Remote Sensing Using Tunable Lasers", K. W. Rothe and H. Walter; in "Tunable Lasers and their Applications," ed. A. Mooradian et al, Springer-Verlag 1976. When laser light sources are employed, ranges of up to 10 km are possible. With optical radar techniques using topographic reflectors or aerosol scattering it is possible to range gaseous absorbers up to a few kilometers from the light source.

The concentrations of gaseous hydrogen fluoride can be monitored using its infra-red absorption. Gaseous hydrogen fluoride molecules are usually in the ground state (no vibrational excitation) and may sequentially absorb light at wavelengths corresponding to transitions to the first, second, third vibrational level etc. These 0→1, 1→2, 2→3, transition frequencies are further split into rotational absorption lines specified as P or R branch transitions. In this specification, the usual convention of describing 0→1 transitions as 1P or 1R lines and 1→2 transitions as 2P or 2R lines is adopted. Transitions such as 0→2 or 0→3 are described as overtones and are very low in intensity. The absorption frequencies characteristic of gaseous hydrogen fluoride have been extensively reported, e.g. R. J. Lovell and W. F. Herget, J. Opt. Soc. Am., 52, 1374 (1962), W. F. Herget et al., ibid., 52, 1113 (1962), D. E. Mann et al., J. Chem. Phys., 34, 420 (1961), D. F. Smith, Spectrochimica Acta, 12, 224 (1958), and G. Guelachvili, Optics Commun., 19, 150 (1976). It has been reported that the absorption peaks are very much broadened and slightly shifted when mixed with gases at atmospheric pressure by J. J. Hinchen, J. Opt. Soc. Am., 64, 1162 (1974) and B. M. Shaw and R. J. Lovell, J. Opt. Soc. Am., 59, 1598 (1969).

Previous optical studies of gaseous hydrogen fluoride pollution have employed the well-known non-dispersive infra-red analysis (hereinafter referred to as NDIR) technique (W. F. Herget et al., Applied Optics, 15, 1222 (1976)), and a Ga-As diode laser absorbed by the 0→3 overtone (V. B. Anzin et al., Soviet J. Quant. Electron. (U.S.A.) 5, 754 (1975)). With the NDIR technique, a path length greater than about 10 m is not feasible and the above paper on NDIR suggests that the sensitivity could be approximately 500 $\mu g.m^{-3}$ gaseous hydrogen fluoride in a path length of 10 m. The technique did not detect levels of 100 $\mu g.m^{-3}$, though it could be of interest for stack gas monitoring. The Ga-As diode laser technique uses kilobar hydrostatic pressures to tune the diode, is difficult to control in frequency, and is not sensitive.

Tunable diode lasers, tuned by current and temperature, are not yet available at frequencies higher than 3750 $cm^{-1}$ and there has been no extension of their availability in this area in the past six years. They do not yet cover the range required for gaseous hydrogen fluoride monitoring (3500–4500 $cm^{-1}$). Other tunable lasers are available: the colour-centre lasers and the spin-flip raman lasers. They are short-lived and require such complexities as nitrogen or helium cryostats and superconducting magnets. All tunable lasers, moreover, would involve formidable problems of stability and resetability.

A hydrogen fluoride laser would be the most unequivocal source for monitoring gaseous hydrogen fluoride through its infra-red absorption. The hydrogen fluoride laser is a chemical laser. Fluorine and hydrogen atoms are generated in a glow discharge (e.g. through sulfur hexafluoride and propane) and combine to form vibrationally excited gaseous hydrogen fluoride which, in a cw laser, then lases on its 3→2, 2→1, 1→0 vibration levels emitting several of the P rotational lines from each level. Of these lines, only the 1P lines are absorbed by gaseous hydrogen fluoride at normal temperatures.

Most reports concerning the atmospheric transmission of gaseous hydrogen fluoride laser outputs are for military applications, e.g. "Handbook of Chemical Lasers", ed. R.W.F. Gross and J. F. Bott, Wiley, 1976, and "Topics in Current Chemistry: Vol 37 Chemical Lasers", K. L. Kompa, Springer-Verlag, 1973. Some reports have referred to atmospheric pollution measurements, e.g., A. S. Gomenyuk et al., Soviet J. Quant. Electron. (U.S.A.), 4, 1001 (1975) and K. W. Rothe and H. Walter, supra. Only one report, A. Tönnissen et al., Applied Physics (Springer-Verlag) 18, 297 (1979), relates to long path gaseous hydrogen fluoride absorption monitoring with a hydrogen fluoride laser.

Tönnissen et al. reported the use of a cw hydrogen fluoride laser to monitor the gaseous hydrogen fluoride concentration in the cell room of the Vereinigten Aluminium Werke smelter. The laser was untuned and lased simultaneously on the 1P (4 to 7) lines and on several 2 P lines. The 2 P lines are not absorbed by gaseous hydrogen fluoride and were used to determine the attenuation due to particulate scattering, carbon dioxide and water vapour. The authors' main problem was the absorption due to water vapour and, to a lesser extent, carbon dioxide. Tönnissen et al., monochromated the output on each line in turn and measured transmission using the usual technique of a chopper and lock-in amplifier, with a retro-reflector at approximately 100 m range. The concentrations of gaseous hydrogen fluoride, and of water vapour, carbon dioxide and particulates, were determined by solving the simultaneous equations with coefficients determined by laboratory measurements of the cross-sections of gaseous hydrogen fluoride, water vapour and carbon dioxide.

The lines available from the type of laser used by Tönnissen et al. are far from ideal regarding their freedom from interference by water vapour. This can be seen with reference to FIG. 3-16 at page 67 of "Infrared Physics and Engineering" J. A. Jamieson et al McGraw-Hill 1963. Tönnissen et al employed lines at 3644.24, 3693.21, 3741,36, 3788.13 and 3833.66 $cm^{-1}$. Most of the precision of their measurement would probably have come from the 3788.13 $cm^{-1}$ line alone. Nevertheless they claimed a precision of 200 $\mu g.m^{-3}$ which would almost meet the SPCC requirements.

The major drawbacks of employing a gaseous hydrogen fluoride laser to monitor the concentration of hydrogen fluoride are:
(i) A gaseous hydrogen fluoride laser requires continuous pumping and a continuous supply of e.g. helium, hydrogen and sulfur hexafluoride;
(ii) Many of the gaseous hydrogen fluoride laser lines suffer excessive interference from water vapour and carbon dioxide;
(iii) The whole system would pose formidable problems in engineering optimisation and maintenance.

Fourier transform infra-red spectrometers ("Introduction to Fourier Transform Spectroscopy" R. J. Bell, Academic Press, 1972) can provide adequate high resolution absorption spectra over long path-lengths but are complex and expensive instruments not suited to rapid data acquisition.

The present invention is based upon the discovery by the present inventor that the helium-neon laser can be employed to generate an infra-red laser beam at a frequency which very nearly coincides with one of the absorption lines of gaseous hydrogen fluoride.

FIG. 15 in "Remote Fourier Transform Infra-red Air Pollution Studies", W. F. Herget and J. D. Brasher, Opt. Eng., 19, 508 (1980) shows a transmission spectrum between 4173 and 4176 $cm^{-1}$ of clean air and of air containing gaseous hydrogen fluoride from a gypsum pond. The strength of the water vapour line at 4174.67 $cm^{-1}$ in the clean air spectrum was matched with that of the same line in the spectrum of the air containing gaseous hydrogen fluoride and the spectra were subtracted to eliminate the effect of the weak water vapour line interference. This revealed a substantially flat base having a peak at a frequency observed to be 4173.9798 $cm^{-1}$ by G. Guelachvili, Optics Communications, 19, 150 (1976) superimposed thereon. The instrumentally broadened peak width observed by Herget and Brasher was 0.15 $cm^{-1}$ full width half maximum, and the substantially flat base line extended from 4173 $cm^{-1}$ and 4176 $cm^{-1}$.

In a helium-neon laser using $^{20}Ne$, it follows from the energy levels reported by C. E. Moore in "Atomic Energy Levels", Circular of NBS No. 467, (U.S. Government Printing Office Washington DC 1949, page 77) that the 3 $p_4$-2 $s_2$ (Paschen Notation) transition emits at 4174.01 $cm^{-1}$ and that a 3 $p_2$-2 $s_2$ transition emits at 4173.13 $cm^{-1}$.

Although Guelachvili, supra, and Moore, supra, taken together would indicate that the mis-match between the gaseous hydrogen fluoride 1 R5 line and the $^{20}$Ne 3 $p_4$-2 $s_2$ He-Ne laser line at 4174.01 $cm^{-1}$ was 0.031 $cm^{-1}$, it has been measured by the present inventor and found to be less than 0.01 $cm^{-1}$. The pressure broadening of the gaseous hydrogen fluoride 1 R5 line by various gases at atmospheric pressure has been reported by R. Beigang et al., Physical Review A 20, 299 (1979) at approximately 0.1 $cm^{-1}$ full width half maximum. Width of the same order would be expected for other media and the resultant pressure broadening of the gaseous hydrogen fluoride absorption line reduces the effect of pressure induced shift of the centre frequency of the gaseous hydrogen fluoride line.

The apparatus and method of the present invention have the major advantage of being able to use helium-neon tubes incorporating well established commercial technology which are filled with any suitable neon isotope.

The apparatus and method of the invention can be operated on any isotope of neon or on mixtures of neon isotopes.

DISCLOSURE OF INVENTION

The present invention therefore provides a method for quantitatively determining the concentration of gaseous hydrogen fluoride in a medium containing gaseous hydrogen fluoride, characterised in that said method comprises combining the results of (a) a measurement of the transmission or absorption of a laser beam at a first frequency corresponding to a neon 3 $p_4$-2

$s_2$ transition through said medium containing gaseous hydrogen fluoride, and (b) a measurement of the transmission or absorption of a laser beam at a second frequency excluding said first frequency, through said medium containing gaseous hydrogen fluoride.

The second frequency should be sufficiently removed from the first frequency not to be significantly absorbed by gaseous hydrogen fluoride and not strongly absorbed by other interfering gases or vapours in the medium. A frequency between 4753 cm$^{-1}$ and 4000 cm$^{-1}$ preferred. A frequency between 4173 cm$^{-1}$ and 4176 cm$^{-1}$ is most preferred. Water vapour is usually encountered as the most interfering gas or vapour when the medium is atmospheric air.

The invention also provides apparatus for quantitatively determining the concentration of gaseous hydrogen fluoride in a medium containing gaseous hydrogen fluoride, characterised in that said apparatus comprises:
 (i) a first source of laser light at a first frequency corresponding to a neon 3 $p_4$–2 $s_2$ transition;
 (ii) first detecting means associated with said first source, located remote from said first source by a suitable path length and being capable of detecting the intensity or absorption of said laser light at said first frequency;
 (iii) a second source of laser light at a second frequency excluding said first frequency, preferably said second frequency is between 4753 cm$^{-1}$ and 4000 cm$^{-1}$ and most preferably between 4173 cm$^{-1}$ and 4176 cm;
 (iv) second detecting means associated with said second source, located remote from said second source by a suitable path length and being capable of detecting the intensity or absorption of said laser light at said second frequency; and
 (v) calculating means associated with the outputs of said first and second detecting means to calculate said concentration;
and wherein said medium containing gaseous hydrogen fluoride is located between said first and second sources and said first and second detecting means so that laser light from said first and second sources passes through said medium containing gaseous hydrogen fluoride to said first and second detecting means.

The laser beam at a first frequency of 3 $p_4$–2 $s_2$ is preferably produced by operating a helium-neon laser with suitable mirrors, e.g., as described by H. Schlemmer et al., Optics Communications, 32, 141 (1980). The second frequency is preferably obtained by operating a helium-neon laser in conjunction with a selective absorber, e.g. laser radiation at a frequency corresponding to the $^{20}$Ne 3 $p_2$–2 $s_2$ transmission may be obtained by incorporating an intra-cavity methane cell in the helium-neon laser as described by K. Bergmann and W. Demtröder, Physics Letters, 29A 94 (1969).

The first frequency is substantially absorbed by low pressure gaseous hydrogen fluoride, high pressure gaseous hydrogen fluoride or gaseous hydrogen fluoride in the presence of other gases or vapours (e.g. air), and the second frequency is substantially unabsorbed by gaseous hydrogen fluoride under the aforementioned conditions.

By using two $^{20}$Ne lasers, with and without an intra-cavity methane cell, the transmission near the peak ($\approx$0.01 cm$^{-1}$ away), and off the peak (approximately 0.9 cm$^{-1}$ away), could be compared thereby compensating for beam divergence, scatter, diffraction and absorption by water vapor and other interfering species.

Laser tubes filled with $^{22}$Ne isotope may also be used. The first frequency ($^{20}$Ne 3 $p_4$–2 $s_2$) would be emitted as set forth above together with $^{22}$Ne 3 $p_4$–2 $s_2$ which is substantially unabsorbed by low pressure gaseous hydrogen fluoride and less absorbed than the first frequency by high pressure gaseous hydrogen fluoride or gaseous hydrogen fluoride plus other gases or vapours. Such fills could lead to a much simpler arrangement in which both the $^{20}$Ne and $^{22}$Ne discharge tubes can share the same laser mirrors.

Embodiments of the invention employing $^{22}$Ne fills alone would employ the configurations described for $^{20}$Ne fills and would find use where sharp resonances of $^{20}$Ne lines with species other than gaseous hydrogen fluoride cause beam transmission problems.

The first and second detecting means may be a pair of detectors or a single detector adapted to detect and discriminate between both frequencies.

Suitable detectors would include, for example, photovoltaic or photoconductive cells, bolometers and optically excited acoustic detectors (spectrophones). The path length chosen will depend on the nature of the detector used and on the expected level of gaseous hydrogen fluoride concentration being determined. When a spectrophone is used the path will usually be less than a few meters, in contrast to the case of the use of the other detectors where high concentrations of gaseous hydrogen fluoride are better determined with short path-lengths whereas low concentrations of gaseous hydrogen fluoride are better determined with long path-lengths. For determinations of gaseous hydrogen fluoride at the levels anticipated in the pot-rooms of aluminium smelters, path-lengths of approximately 800 m would be required.

Calculations show that for gaseous hydrogen fluoride in air at 100 $\mu$ g.m$^{-3}$ the $^{20}$Ne 3$p_4$–2 $s_2$ laser beam would be attenuated to approximately half intensity in a distance of approximately 800 m. Over this path length assuming a detection accuracy of 2%, the range of monitoring would be to a maximum of approximately 500 $\mu$g.m$^{-3}$, with an estimated accuracy of $\pm$3 $\mu$g.m$^{-3}$ or $\pm$2% whichever is greater.

BRIEF DESCRIPTION OF DRAWINGS

Preferred embodiments of the invention are described in the following Examples with reference to the accompanying drawings in which.

In the drawing like numbers refer to like parts.

BEST MODE OF CARRYING OUT THE INVENTION

EXAMPLE 1

Figure 1:
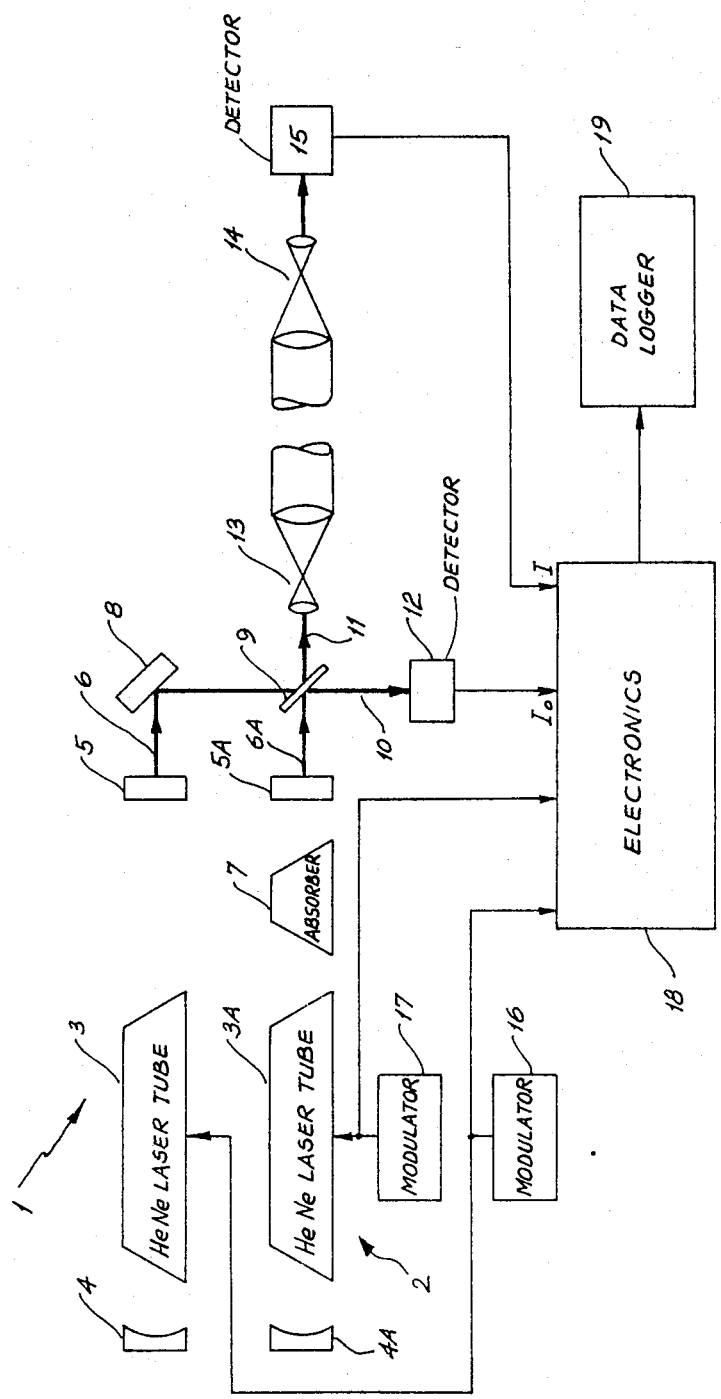
FIG. 1 represents a first preferred embodiment of an apparatus of the invention.

In the embodiment of the invention illustrated in FIG. 1 two lasers 1 and 2 are both operated with $^{20}$Ne fills.

The laser 1 consists of a helium-neon discharge tube 3, preferably a sealed tube, with its associated optical cavity comprising mirror 4 and partially reflecting mirror 5 suitably mounted and spaced. The mirrors 4 and 5 allow the device to lase on the $^{20}$Ne 3 $s_2$–3 $p_4$, 3 $p_4$, 3 $p_4$–2 $s_2$, 2 $s_2$–2 $p_4$ cascade sequence and mirror 5 which is semi-transparent at the 3 $p_4$–2 $s_2$ frequency provides the lasers useful output beam 6.

The laser 2 has a similar optical cavity defined by discharge tube 3A and mirrors 4A and 5A but with the addition of an intra cavity frequency selective absorber 7 (which may, for example, be a Brewster windowed cell containing methane gas at a few kilopascal pressure) which forces the laser 2 to lase on the $^{\cdot}$Ne 3 $s_2$–3 $p_2$, 3 $p_2$–2 $s_2$, 2 $s_2$–2

4, cascade sequence rather than the other, higher gain cascade on which the laser 1 operates. The semi-transparent mirror 5A allows the laser 2 to produce an output beam 6A of which the 3 $p_2$–2 $s_2$ is the useful component.

The output beams 6 and 6A of the lasers 1 and 2 respectively are combined using mirror 8 and splitter 9 into beams 10 and 11, the inensity of beam 10 ($I_o$) sampled by a detector 12 adapted with filters (not shown) to respond preferentially to $^{20}$Ne 3 $p_4$–2 $s_2$ and $^{20}$Ne 3 $p_2$–2 $s_2$ inputs. The beam 11 is conditioned for transmission over a long path by expansion through a telescope 13.

At the remote end of the long path the beam is collected using a suitable telescope 14 and the received intensity (I) is measured by the remote detector 15 adapted with a filter (not shown) to respond preferentially to $^{20}$Ne 3 $p_4$–2 $s_2$ and $^{20}$Ne 3 $p_2$–2 $s_2$ inputs.

The lasers 1 and 2 are modulated by modulators 16 and 17 in such a manner than the detection electronics are capable of distinguishing and separately treating the signals therefrom. The electronics 18 compares the long path transmission, as evidenced by $I_o$ and I for the pair of wavelengths, calculates $\ln(I_o/I)$ for the first frequency and subtracts from it $\ln(I_o/I)$ for the second frequency thus producing on output proportional to the average gaseous hydrogen fluoride concentration over the path length studied. The output may be displayed or stored on a recorder or data logger 19.

EXAMPLE 2

Figure 2:
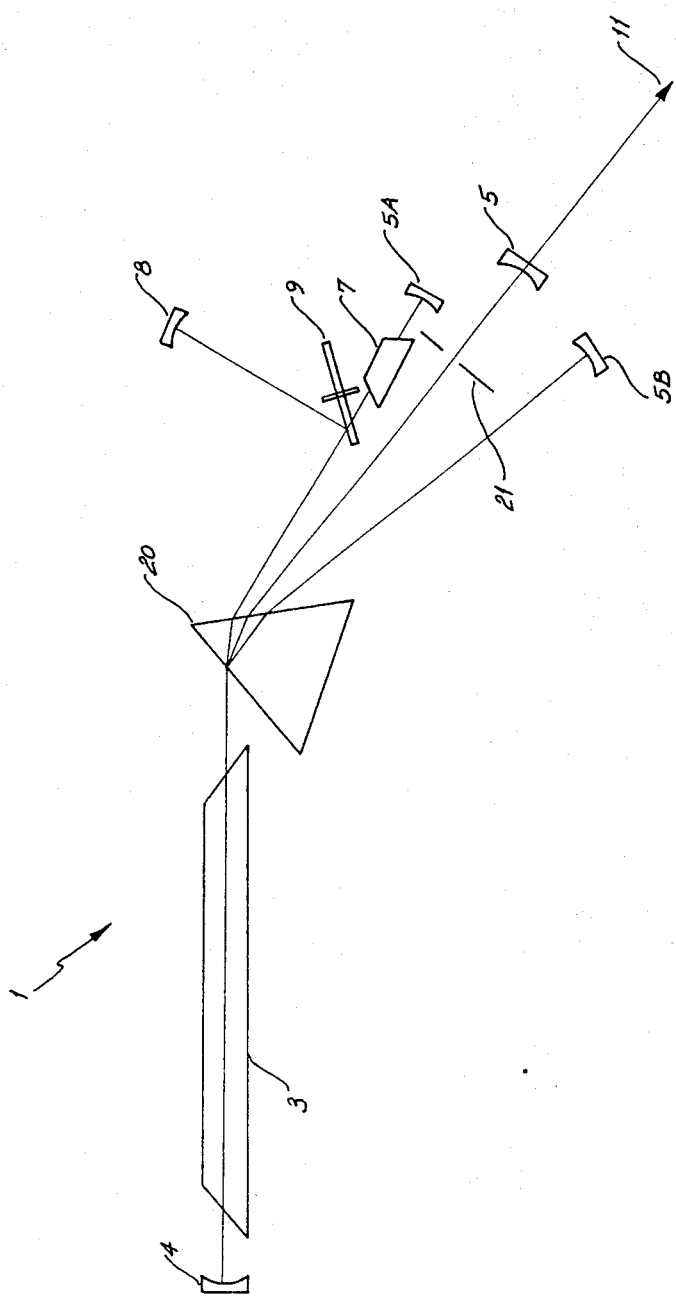
FIG. 2 represents a second preferred embodiment of the apparatus of the invention.

In the embodiment of the invention, illustrated in FIG. 2, the laser 1 consists of a helium-neon discharge tube 3 with a frequency dispersive optical cavity comprising a broad band mirror 4 at one hand and a Brewster angle prism 20 at the other end complete with individual mirrors 5A, 5 and 5 B for the 3 $s_2$14 3 $p_2$, (3 $p_4$–2 $s_2$ and 3 $p_2$–2 $s_2$), and 2 $s_2$–2 $p_4$ transitions respectively. Mirror 5 is partially transmitting. This arrangement would allow optimum mirrors to be employed and would result in higher power more directionally stable 3 $p_4$–2 $s_2$ and 3 $p_2$–2 $s_2$ output beam 11.

FIG. 2 illustrates a mirror surfaced chopper 9 in the 3 $s_2$–3 $p_4$ cavity defined by broad band mirror 4 and mirror 8. The apertures in the mirror surfaced chopper 9 allow the beam to pass through a methane cell 7 to a subsidiary mirror 5 A for the 3 $s_2$—3 $p_2$ transition to effect switching between the 3 $p_4$–2 $s_2$ and 3 $p_2$–2 $s_2$ transitions.

FIG. 2 also illustrates a preferred aperture 21 in the (3 $p_4$–2 $s_2$ and 3 $p_2$–2 $s_2$) cavity to permit $TEM_{oo}$ mode operation without influencing the transverse modes of the other lasing transitions. This modification will lead to more directionally stable outputs. The laser apparatus depicted in FIG. 2 is employed with a telescope and detector or detectors to as to FIG. 1 complete the apparatus of the invention.

In Example 3 which follows, two helium-neon laser tubes are operated inside a single optical cavity, one tube emitting on the $^{22}$Ne 3 $p_4$–2 $s_2$ frequency and the other on the $^{20}$Ne 3 $p_4$–2 $s_2$ line. This permits small, rigid and light weight laser resonators to be used and the beam combiners and moving parts described in relation to FIG. 2 would not be required. The two laser tubes can be alternately switched on and off or can employ partial internal modulation of the dischargers at two different frequencies to allow the collinear copropagating beams to be distinguished. Available data indicates that the $^{22}$Ne 3 p–2 $s_2$ frequency lies about 0.03 cm$^{-1}$ above the $^{20}$Ne 3 $p_4$–2 $s_2$ frequency.

EXAMPLE 3

Figure 3:
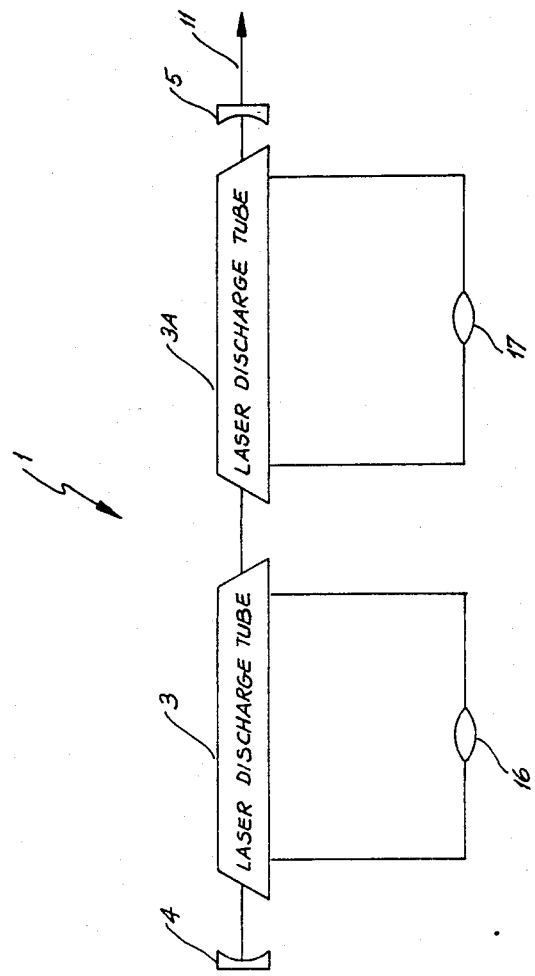
FIG. 3 represents a third preferred embodiment of an apparatus of the invention.

FIG. 3 illustrates an embodiment of the invention in which the laser 1 is made up of two collinear helium-neon discharge tubes 3 and 3A which share a common optical cavity between two broad band mirrors 4 and 5 of which mirror 5 is partially transparent for the 3 $p_4$–2 $s_2$ frequencies.

The first frequency ($^{20}$Ne 3 $p_4$–2 $s_2$) is produced by tube 3 which predominantly contains the 20 isotope of neon and the second frequency ($^{22}$Ne 3 $p_4$–2 $s_2$) is produced by tube 3A which predominantly contains the 22 isotope of neon. The discharges of tubes 3 and 3A are modulated at rates $\omega_1$ and $\omega_2$ at 16 and 17 respectively so as to allow the $^{20}$Ne laser emission to be distinguished from the $^{22}$Ne laser emission in the output beam 11. The rates $\omega_1$ and $\omega_2$ were preferably non-harmonically related.

The two collinear, copropagating beams are directed through the path to be studied and detected by a detecting means capable of distinguishing between the separately modulated output frequencies.

This embodiment will allow a compact laser structure to be used and will provide better directional stability of the output beams. The laser transitions are high in gain allowing the use of simpler and cheaper mirrors 4 and 5 in an easily adjustable optical cavity.

The laser apparatus depicted in FIG. 3 is employed with a telescope and detector or detectors to complete the apparatus of the invention.

The apparatus and method of the present invention can also be applied to build an instrument for flow-sampling a medium to determine gaseous hydrogen fluoride concentration. A "spectrophone" ("Optoacoustic Spectroscopy and Detection" Ed. Yoh-Han Pao, Academic Press, 1977) could be installed in the switched (3 $p_4$–2 $s_2$ and 3 $p_2$–2 $s_2$) beam illustrated in FIG. 1 (intra-cavity or extra-cavity) and the medium to be analysed for gaseous hydrogen fluoride could flow slowly through it. This application of the present invention would enable a level of sensitivity in the detection of gaseous hydrogen fluoride to be attained which would be of interest in environmental studies.

EXAMPLE 4

Figure 4:
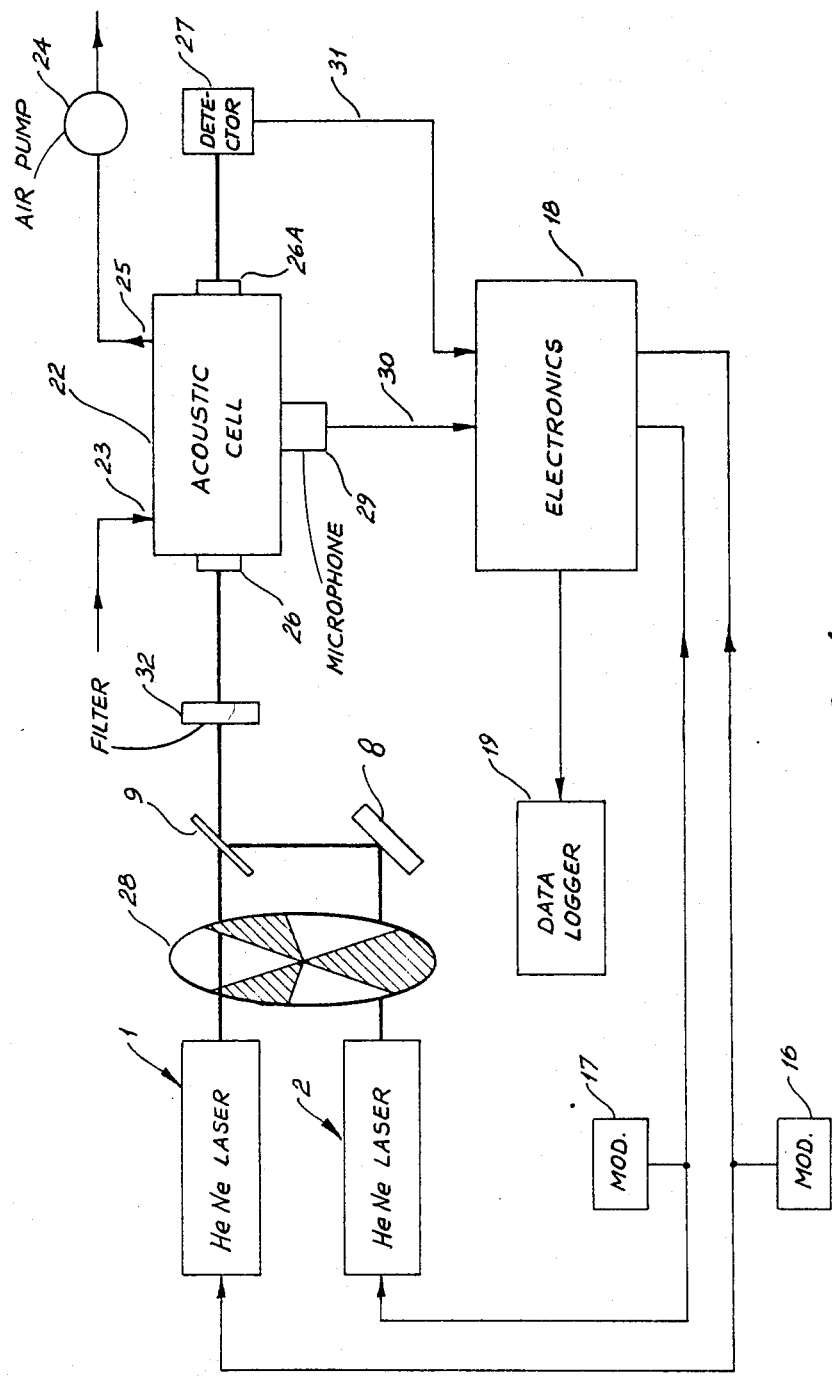
FIG. 4 represents a fourth preferred embodiment of an apparatus of the invention.

FIG. 4 shows an example of the use of a spectrophone for local determination of gaseous hydrogen fluoride concentration.

Air containing gaseous hydrogen fluoride is drawn through an acoustic cell 22 at inlet 23 by an air pump 24 operating at outlet 25. The acoustic cell is fitted with windows 26 and 26A which allow laser beams from two lasers 1 and 2 to pass through the cell. The length of the cell and the expected gaseous hydrogen fluoride concentration are such that the energy absorbed inside the cell is such a small (<1%) fraction of the incident energy that the beams which reach the photoconductive detector 27 accurately represent the intensity of the beams incident on the cell.

The two lasers 1 and 2 generate $^{20}$Ne 3 p$_4$–2 s$_2$ and $^{20}$Ne 3 p$_2$–2 s$_2$ output respectively and the optical chopper 28 alternately allows the beams from the first and second laser to pass through the acoustic cell. The laser beams are combined using suitable mirror 8 and splitter 9 so as to be collinear and co-propagating. Further, lasers 1 and 2 are amplitude modulated by modulators 16 and 17 respectively at frequencies much higher than the chopper rate and which modulation frequencies are suited to the dimensions of the acoustic cell 22 and the frequency response of the microphone 29 which produces an output proportional to the product of the incident laser beam intensity and the probability of absorption of that wavelength inside the acoustic cell.

When the microphone output signal 30 is divided by the photo conductive detector output 31 the resulting signal is proportional to the gaseous hydrogen fluoride concentration with an added noise component caused by window absorbtion and background acoustic noise etc.

Since the $^{20}$Ne 3 p$_2$–2 s$_2$ frequency is unabsorbed by gaseous hydrogen fluoride the acoustic cell 22 produces an output due only to noise sources such as window losses and background acoustic noise when that frequency traverses the cell.

By alternately irradiating the acoustic cell through an optical filter 32 which passes only the $^{20}$Ne 3 p$_4$–2 s$_2$ and $^{20}$Ne 3 p$_2$–2 s$_2$ frequencies and by using suitable calculating means 18 on the alternating signals the noise contributions to the output may be greatly reduced, and an output voltage proportional to the gaseous hydrogen fluoride concentration in the sampled air may be produced. The output may be displayed or stored on a recorder or data logger 19.

Whilst the foregoing description is directed to determining gaseous hydrogen fluoride concentration in the atmosphere, the method and apparatus are suitable for determining gaseous hydrogen fluoride concentrations in other media and also where the medium consists of pure gaseous hydrogen fluoride alone at atmospheric, sub-atmospheric and super-atmospheric pressure, and modifications obvious to those skilled in the art may be made thereto without departing from the scope of the present invention.

I claim:

1. A method for quantitatively determining the concentration of gaseous hydrogen fluoride in a medium containing gaseous hydrogen fluoride, characterised in that said method comprises combining the results of (a) a measurement of the transmission or absorption of a laser beam at a first frequency corresponding to a neon 3 p$_4$–2 s$_2$ transition through said medium containing gaseous hydrogen fluoride, and (b) a measurement of the transmission or absorption of a laser beam at a second frequency excluding said first frequency, through said medium containing gaseous hydrogen fluoride.

2. The method as defined in claim 1, characterised in that said second frequency is sufficiently removed from said first frequency not to be significantly absorbed by gaseous hydrogen fluoride and not strongly absorbed by other interfering gases or vapours in said medium.

3. The method as defined in claim 1 or claim 2 characterised in that said second frequency excluding said first frequency is between 4753 cm$^{-1}$ and 4000 cm$^{-1}$.

4. The method as defined in claim 3, characterised in that said second frequency excluding said first frequency is between 4173 cm$^{-1}$ and 4176 cm$^{-1}$.

5. The method as claimed in claim 4, characterised in that said medium is atmospheric air.

6. An apparatus for quantitatively determining the concentration of gaseous hydrogen fluoride in a medium containing gaseous hydrogen fluoride, characterised in that said apparatus comprises:
   (i) a first source of laser light at a first frequency corresponding to a neon 3 p$_4$–2 s$_2$ transition;
   (ii) first detecting means associated with said first source, located remote from said first source by a suitable path length for detecting the intensity or absorption of said laser light at said first frequency;
   (iii) a second source of laser light at a second frequency excluding said first frequency;
   (iv) second detecting means associated wth said second source, located remote from said second source by a suitable path length for detecting the intensity or absorption of said laser light at said second frequency; and
   (v) calculating means associated with the outputs of said first and second detecting means to calculate said concentration;
and wherein said medium containing gaseous hydrogen fluoride is located between said first and second sources and said first and second detecting means so that laser light from said first and second sources passes through said medium containing gaseous hydrogen fluoride to said first and second detecting means.

7. The apparatus as defined in claim 6, characterised in that said first source is a helium-neon laser.

8. The apparatus as defined in claim 7 characterised in that said helium-neon laser includes $^{20}$Ne or $^{22}$Ne.

9. The apparatus as defined in claim 6, characterised in that said second source is a helium-neon laser in conjunction with a selective absorber.

10. The apparatus as defined in claim 9, characterised in that said helium-neon laser includes $^{20}$Ne and said selective absorber is an intra-cavity methane cell.

11. The apparatus as defined in claim 9, characterised in that said second source is a $^{22}$Ne helium-neon laser.

12. The apparatus as defined in claim 6, characterised in that said first and second detecting means comprise a pair of detectors or a single detector for detecting and discriminating between the frequencies of said first and second sources.

13. The apparatus as defined in claim 12, characterised in that said detectors are photovolataic or photoconductive cells, bolometers or optically excited acoustic detectors.

* * * * *